United States Patent [19]

Trost et al.

[11] 4,007,211
[45] Feb. 8, 1977

[54] CONVERSION OF ORGANIC CARBOXYLIC ACID TO CORRESPONDING KETONE WITH LOSS OF CARBON ATOM

[75] Inventors: Barry M. Trost; Yoshinao Tamaru, both of Madison, Wis.

[73] Assignee: Wisconsin Alumni Research Foundation, Madison, Wis.

[22] Filed: May 19, 1975

[21] Appl. No.: 578,533

[52] U.S. Cl. .................. 260/397.3; 260/514 G; 260/586 F; 260/397.1; 260/239.55 C
[51] Int. Cl.² .................................. C07J 5/00
[58] Field of Search .............. 260/397.3, 514, 586

[56] References Cited

UNITED STATES PATENTS 3,794,669   2/1974   Wynberg et al. ............... 260/397.2

*Primary Examiner*—Elbert L. Roberts
*Attorney, Agent, or Firm*—McDougall, Hersh & Scott

[57] ABSTRACT

A method for converting organic carboxylic acid or esters to an organic ketone with the loss of the carboxylic acid carbon atom in which the organic carboxylic acid or its ester is first subjected to a sulfenylation reaction for positioning an —SR group alpha to the carboxylic acid group and then subjecting the sulfenylated product to oxidative decarboxylation.

19 Claims, No Drawings

CONVERSION OF ORGANIC CARBOXYLIC ACID TO CORRESPONDING KETONE WITH LOSS OF CARBON ATOM

This invention relates to a procedure for converting an organic carboxylic acid or derivative to an organic ketone with loss of the carboxyl or derivative group.

The conversion of an organic carboxylic acid (or derivative) to a ketone, with loss of a carbon atom, represents an important objective in organic chemistry. Various approaches have been investigated by the most highly skilled in the art as indicated by the following:

a. P. Barbier and R. Locquin, C. R. Acad. Sci., 156, 1443 (1913);
b. H. Wieland, Z. Physiol. Chem., 161, 80 (1926);
c. C. Meystre, H. Frey, A. Wettstein, and K. Miescher, Helv. Chim. Acta, 27, 1815 (1944);
d. W. M. Hoehn and H. L. Mason, J. Amer. Chem. Soc., 60, 1493 (1938);
e. G. Lehman, L. Koppe, and G. Hilgetag, J. pradkt. Chem., 32, 217 (1966);
f. J. Meinwald, A. Lewis, and P. G. Gassman, J. Amer. Chem. Soc., 84, 977 (1962);
g. Y. Yanuka, R. Katz, and S. Sarel, Tetrahedron Lett., 1725 (1968);
h. Y. Yanuka, R. Katz, and S. Sarel, Chem. Commun., 851 (1968);
i. M. Fetizon, F. J. Kakis, and V. Ignatiadow-Ragoussis, J. Org. Chem., 38, 1732 (1973);
j. N. L. Allinger, T. J. Walter, and M. G. Newton, J. Amer. Chem. Soc., 96, 4588 (1974).

This type of degradation represents an important tool in the structural elucidation of natural products. It allows carboxyl acid derivatives to serve as synthetic equivalents of other structural fragments. For example, acrylic acid becomes an equivalent of ketene; carboxylic acid becomes acyl anion equivalents; malonic acid becomes an equivalent of a carbonyl dianion, etc.

It is an object of this invention to provide a method of conversion of carbocylic acids and their derivatives to ketones with the loss of a carbon atom, in which the conversion can be carried out in a minimum number of reaction steps and at high yield, thereby to provide a commercially acceptable procedure for carrying out the desired conversion.

Briefly described, the process of this invention comprises a first sulfenylation of the organic carboxylic acid compound (acid or ester from which the ester can be hydrolyzed off to form the acid), as represented by the following equation (1), followed by oxidative decarboxylation of the resulting compound, as represented by the following equation (2):

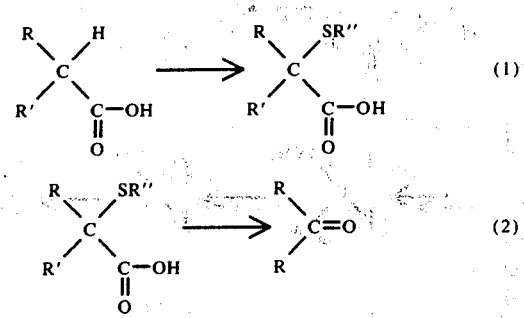

in which R and R' together or separately represent an organic group, which can be the same or different, saturated or unsaturated, halogen, amine or amido substituted (except that the amine substituent should not have a free hydrogen atom), aliphatic, aromatic, condensed aromatic, heterocyclic, cycloaliphatic, and the like group in which the aliphatic group is an alkyl, alkenyl, alkynyl group such as methyl, ethyl, isopropyl, propyl, butyl, isobutyl, t-butyl to $C_{18}$ alkyl; alkenyl, propenyl, butenyl, its $C_{18}$ alkenyl, butnyl, its $C_{18}$ alkynyl group, halogen amino or amido substituted alkyl, alkenyl, alkynyl or cycloalkyl groups, as recited above, such as chloro, bromo, iodo, amido and amino derivatives thereof; aryl or alkaryl groups, such as benzyl, tolyl, styryl, anthracyl, ethyl benzyl and the like; alicyclic groups such as cyclopropyl, cyclopentyl, cyclohexyl and halogen, amino and amido substituents thereof; heterocyclic groups such as pyridyl, furanyl, thiophenyl, pyrimidyl, quinolyl; and hydrogen, except that both R and R' cannot be hydrogen; R" represents an alkyl, cycloalkyl, aryl, alkaryl group of the type corresponding to R and R', without limitation as to the size of the alkyl, aryl, arylalkyl or cycloalkyl group of the thio group except that R" should not be alkenyl or alkynyl.

Sulfenylation of the carboxylic acid compound is carried out by reaction with two equivalents of lithium, diisopropyl amide to form the corresponding dianion, followed by the addition of the disulfide of the R" group. The sulfenylation reaction, carried out at a temperature within the range of 0° to −20° C for from 1 to 3 hours, proceeds practically quantitatively. For dialkylcarboxylic acid in which both R and R' are alkyl, the addition of HMPA for the neutralization (dianion reaction) and the sulfenylation is desirable. The sulfenylation reaction can be carried out on the corresponding ester followed by hydrolyzing off the ester to provide the α-thio acid.

The oxidative decarboxylation of the formed sulfenylated acid, generically referred to as the α-thio or alkyl thio carboxylic acid, to the ketone, is carried out by addition of N-chlorosuccinimide or other positive halogen source, such as N-chlorophthalimide, tert-butylhypochlorite or sodium hypochlorite, or by the addition of an alkali metal periodate such as sodium meta periodate, at room temperature to a mixture of the sulfenylated acid and sodium bicarbonate in an alcohol, such as methanol, ethanol, t-butanol or other $C_1$ to $C_8$ alcohol. It is preferred to carry out the above reaction with the alcohol in an anhydrous state. The reaction occurs with the evolution of carbon dioxide.

Aqueous work-up allows isolation of the ketal which readily hydrolyzes to the corresponding ketone with an aqueous acid such as hydrochloric acid.

Examples of the various applications that can be made of the process of this invention are summarized in the following tabulation which gives the carboxylic acid, the sulfenylation reaction conditions for the various parent compounds, the corresponding sulfenylated reaction product, the conditions for the oxidative decarboxylation reaction that is performed on the various sulfenylated (α-thio) compounds and the resulting ketone.

Table 1. Oxidative Decarboxylation

| Entry No. | Acid | Sulfenylation[a] Temp., Time(min) | Sulfenylated acid | Oxidation Time (hr) | Ketone | Overall isolated yield from starting acid |
|---|---|---|---|---|---|---|
| 1 | (1-naphthyl-2-yl)CH(CH$_3$)CO$_2$H | −20°, 20[b]; 0°, 30 | (naphthyl)C(SCH$_3$)(CH$_3$)CO$_2$H[d] | 1.25[i] | 2-acetonaphthone | 64%[m] |
| 2 | Ph$_2$CHCO$_2$H | −20°, 25[b]; 0°, 25 | Ph$_2$C(SCH$_3$)CO$_2$H[e] | 1.5[j] | Ph$_2$CO | 57%[m] |
| 3 | bicyclic alkene-CO$_2$H | 0°, 40[c] | bicyclic alkene-C(SCH$_3$)CO$_2$H[f] | 1.5–2.5[i] | bicyclic alkene ketone | 44%[n] |
| 4 | ketal-cyclohexyl-cyclohexyl-CO$_2$H | 0° 30[c] | ketal-cyclohexyl-cyclohexyl(SCH$_3$)CO$_2$H[g] | 1.5[i] | O=cyclohexyl-cyclohexyl=O | 78%[m] |
| 5 | (CH$_3$O)$_2$-cyclohexyl-cyclohexyl-CO$_2$CH$_3$ | −20°, 30[b]; 0°, 30; rt, 5 | O=cyclohexyl-cyclohexyl(SCH$_3$)CO$_2$H[h] | 3[i] | O=cyclohexyl-cyclohexyl=O[k] | 69%[m] |
| 6 | CH$_3$O-tricyclic alkene-CO$_2$H | 0°, 50[c] | CH$_3$O-tricyclic alkene(SCH$_3$)CO$_2$CH | 2[i] | CH$_3$O-tricyclic alkene=O | 62–76%[n] |

[a] Dianion generation accomplished utilizing 2 eq of lithium diisopropylamide at between 0° and −20° for 1–3 hr.
[b] Solvent: THF.
[c] Solvent: THF-HMPA.
[d] Isolated sample had mp 109–114°.
[e] Isolated sample had mp 178–179°.
[f] Isolated sample had mp 104–113°.
[g] Isolated sample had mp 149–150°.
[h] Work-up of the sulfenylation reaction effected hydrolysis of the ketal. Hydrolysis of the ester was accomplished by utilizing aqueous potassium hydroxide in refluxing ethylene glycol.
[i] Solvent: ethanol.
[j] Solvent: t-butanol.
[k] Identified by comparison to an authentic sample.
[l] Vpc analysis indicates greater than 96% purity of indicated isomer.
[m] Intermediate sulfenylated acid purified prior to oxidative elimination.
[n] Intermediate sulfenulated acid not purified prior to oxidative elimination.

It will be seen from the Examples 1 to 6 that the invention has been successfully practiced, with good yield, with the α,α-diaryl, arylalkyl, dialkyl carboxylic acid. The presence of unsaturated olefinic groups (Examples 3 and 6) or keto groups (Example 5) do not interfere with the oxidative decarboxylation reaction. Example 5 also illustrates the availability of the desired intermediate by hydrolysis of the sulfenylated ester.

The mechanistic rationale for the oxidative decarboxylation reaction of this invention can perhaps best be explained by the following equation in which SCH$_3$ is used to represent the thioalkyl group and which suggests chlorination at sulfur rather than at the carboxylate anion.

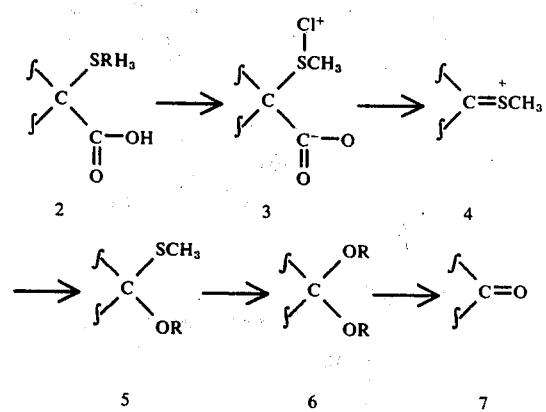

The presence of the intermediate 3 is supported by the observation of alkoxy displacement products 8 and 9 which are obtained when the more nucleophilic alcohols were employed as solvents. This pathway is precluded when ethanol is used as the solvent in the naphthyl system

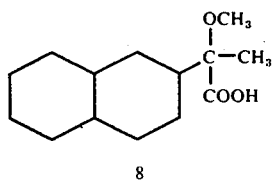

8 and t-butanol is used as the solvent with the benzhydryl system

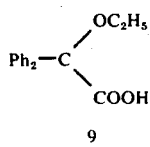

9

The use of a somewhat nucleophilic alcohol to trap the sulfenium ion 4 is desired when the α-carbon bears a hydrogen group. Ethanol represents the preferred solvent for carrying out the oxidative decarboxylation reaction except with the diaryl compounds wherein t-butanol represents the preferred alcohol.

One equivalent of the halogen source (N-chlorosuccinimide) can be used in the oxidative decarboxylation reaction but it is preferred to have additional equivalents and preferably two equivalents for conversion of equation 5 to equation 6. The alcohol protects the ketal 6 and removal to form the ketone 7.

Example 6 illustrates the utilization of the process of this invention for the preparation of the important Corey Prostaglandin intermediate.

Utilizing the process of this invention, the important compound progesterone can be prepared from bis-nor cholan aldehyde 10 in accordance with the following reaction.

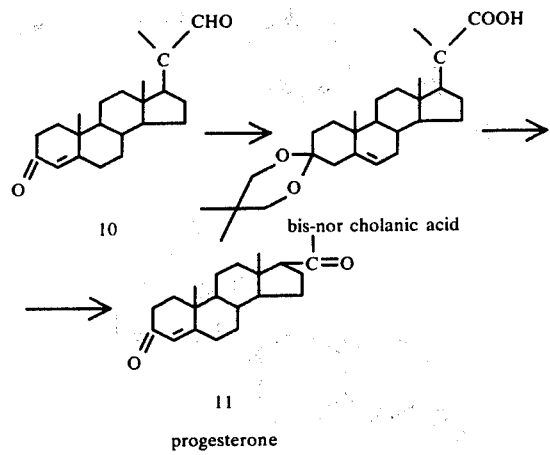

The further advantages of the method of this invention are evidenced by the synthesis of the important Corey prostaglandin intermediate in accordance with Example 6, using acrylic acid as the ketene equivalent. The preparation of the bicycloheptane, identified as the starting compound in Example 6, recognizes the excellent dienophilic properties of the acrylic acid and minimizes base catalyzed isomerization of the intermediate 5-monoalkylated cyclopentadiene. Chromatographic analysis of the Corey prostaglandin intermediate produced (silicon oil DC 710 column) indicates greater than 96% isomeric purity. The novel use of acrylic acid in the Diels Alder reaction used to prepare the parent compound may be represented by the following equations:

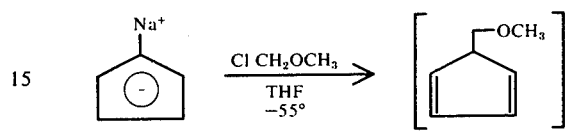

The novel reaction of the above with acrylic acid in a Diels Alder reaction is illustrated by the following:

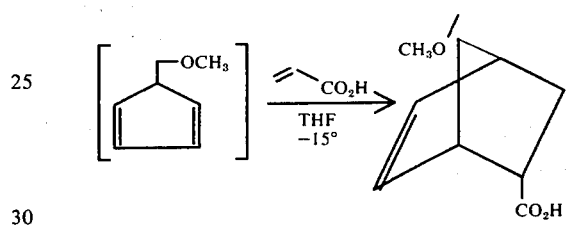

The product identified as 7-methoxymethylbicyclo[2,2,1]-hept-5-ene-2-carboxylic acid is reacted in accordance with Example 6 to produce the prostanoid intermediate identified as 7 methoxymethylbicyclo[2,2,1]-hept-5-ene-2-one.

It will be understood that changes may be made in the details of formulation and operation without departing from the spirit of the invention, especially as defined in the following claims.

We claim:
1. The method of converting an alpha thio carboxylic acid compound having the general formula

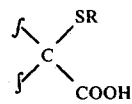

to the corresponding ketone having the general formula

wherein the carboxylic carbon is removed and in which R is an organic group other than an alkenyl or alkynyl group comprising subjecting the alpha thio carboxylic acid compound to oxidative decarboxylation by reaction of the alpha thio carboxylic acid compound with a positive halogen source.

2. The method as claimed in claim 1 in which the oxidative decarboxylation reaction is carried out in the presence of alkali metal carbonate in a $C_1$ to $C_8$ alcohol.

3. The method as claimed in claim 2 in which the oxidative decarboxylation reaction is carried out at ambient temperature.

4. The method as claimed in claim 2 in which the halogen source is selected from the group consisting of N-chlorosuccinimide, N-chlorophthalimide, tert-butylhypochlorite and alkali metal hypochlorite and alkali metal periodate.

5. The method as claimed in claim 2 in which at least one equivalent of the halogen source is reacted per equivalent of carboxylic acid.

6. The method as claimed in claim 2 in which two equivalents of the halogen source are reacted per equivalent of carboxylic acid.

7. The method for conversion of an organic carboxylic acid or ester to the corresponding organic ketone with the loss of a carbon atom comprising sulfenylation of the carboxylic acid or ester compound to form a corresponding alpha thio derivative of the organic carboxylic acid or ester and then subjecting the sulfenulated compound to oxidative decarboxylation whereby the alpha thio and carboxylic acid group are replaced by a ketone group in accordance with the following equations:

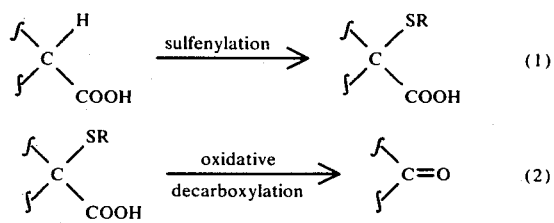

in which R is any organic group other than alkenyl and alkynyl, in which the sulfenylation of the carboxylic acid or ester is carried out by reacting the dianion of the carboxylic acid or ester with an organic disulfide to form the corresponding alpha thio carboxylic acid compound and in which the oxidative decarboxylation is carried out by reacting the alpha thio carboxylic acid with a positive halogen source.

8. The method as claimed in claim 7 in which the dianion is formed by reacting the carboxylic acid or ester with lithium isopropylamide.

9. The method as claimed in claim 8 in which the reaction is carried out at a temperature within the range of 0° to −20° C.

10. The method as claimed in claim 7 in which, when the sulfenylation reaction is carried out on the carboxylic acid ester, the ester group is hydrolyzed off to form the corresponding carboxylic acid before being subjected to the oxidative decarboxylation reaction.

11. The method as claimed in claim 7 in which the oxidative decarboxylation reaction is carried out by reacting the sulfenylated compound with a positive halogen source and alkali metal carbonate in a $C_1$ to $C_8$ alcohol.

12. The method as claimed in claim 11 in which the oxidative decarboxylation reaction is carried out at ambient temperature.

13. The method as claimed in claim 11 in which the positive halogen source is selected from the group consisting of N-chlorosuccinimide, N-chlorophthalimide, tert-butylhypochlorite and alkali metal hypochlorite.

14. The method as claimed in claim 11 in which two equivalents of the positive halogen source are reacted per equivalent of carboxylic acid.

15. The method for preparing progesterone comprising the steps of subjecting bis-nor cholanic acid to sulfenylation to provide an -SR group alpha to the carboxylic acid group in accordance with the following equation:

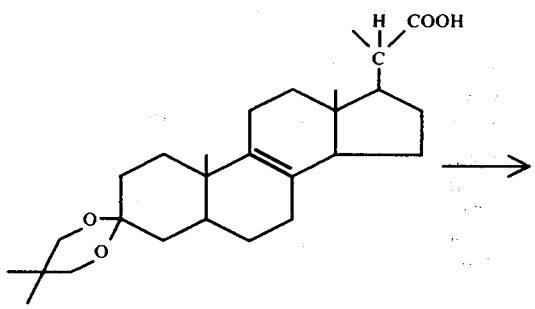

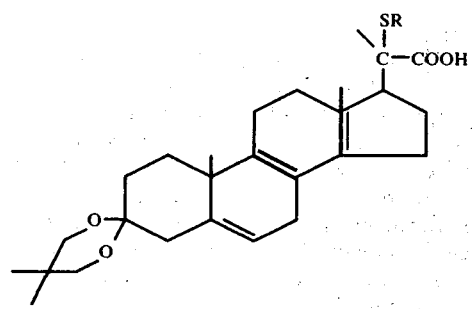

and then subjecting the sulfenylated product to oxidative decarboxylation in accordance with the following equation:

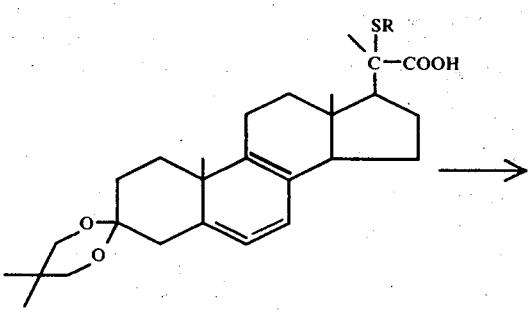

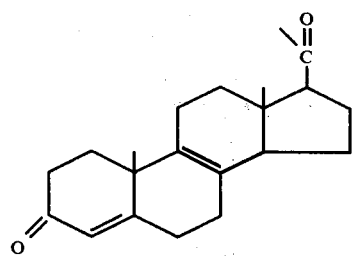

16. The method as claimed in claim 1 in which the oxidative decarboxylation reaction is carried out by reacting the alpha-thio carboxylic acid compound with an alkali metal periodate and an alkali metal carbonate in a $C_1 - C_8$ alcohol.

17. The method for preparing the Corey prostaglandin intermediate 7-methoxymethylbicyclo [2,2,1]-hept-5-ene-2-one by sulfenylation of 7-methoxymethyl-bichclo [2,2,1-hept-5-ene-2 carboxylic acid] to form the corresponding alpha-thio carboxylic acid compound and then subjecting the alpha-thio carboxylic acid compounds to oxidative decarboxylation to produce 7-methoxymethylbicyclo [2,2,1]-hept-5-ene-2-one.

18. The method of producing the 7-methoxymethyl-bicyclo [2,2,1]-hept-5-ene-2 carboxylic acid by Diels Alder reaction with acrylic acid of the compound represented by the equation

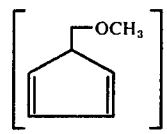

19. The method as claimed in claim 1 in which the oxidative decarboxylation reaction is carried out by reacting the alpha-thio carboxylic acid compound with an alkali metal periodate in a $C_1 - C_8$ alcohol.

UNITED STATES PATENT OFFICE
CERTIFICATE OF CORRECTION

Patent No. 4,007,211   Dated February 8, 1977

Inventor(s) Barry M. Trost et al

It is certified that error appears in the above-identified patent and that said Letters Patent are hereby corrected as shown below:

Column 1, before the first paragraph, insert --

The Government has rights in this invention pursuant to Grant No. MPS-71-03396 awarded by the National Science Foundation and NIH Grant No. 5-R01-GM-13598 awarded by the Department of Health, Education, and Welfare.

Signed and Sealed this

Third Day of May 1977

[SEAL]

Attest:

RUTH C. MASON  
Attesting Officer

C. MARSHALL DANN  
Commissioner of Patents and Trademarks